(12) United States Patent
Sampayan et al.

(10) Patent No.: US 12,415,092 B2
(45) Date of Patent: *Sep. 16, 2025

(54) FLASH RADIOTHERAPY ACCELERATOR SYSTEM

(71) Applicants: Lawrence Livermore National Security, LLC, Livermore, CA (US); Opcondys, Inc., Manteca, CA (US)

(72) Inventors: Stephen E. Sampayan, Manteca, CA (US); George James Caporaso, East Quogue, NY (US); Yu-Jiuan Chen, Fremont, CA (US); Kristin Cortella Sampayan, Manteca, CA (US)

(73) Assignees: Lawrence Livermore National Security, LLC, Livermore, CA (US); Opcondys, Inc., Manteca, CA (US)

( * ) Notice: Subject to any disclaimer, the term of this patent is extended or adjusted under 35 U.S.C. 154(b) by 655 days.

This patent is subject to a terminal disclaimer.

(21) Appl. No.: 17/575,074

(22) Filed: Jan. 13, 2022

(65) Prior Publication Data

US 2022/0219014 A1 Jul. 14, 2022

Related U.S. Application Data

(60) Provisional application No. 63/136,645, filed on Jan. 13, 2021.

(51) Int. Cl.
*H05H 7/00* (2006.01)
*A61N 5/10* (2006.01)
(Continued)

(52) U.S. Cl.
CPC ......... *A61N 5/1048* (2013.01); *A61N 5/1078* (2013.01); *H05H 7/04* (2013.01);
(Continued)

(58) Field of Classification Search
CPC ........ H05H 7/22; H05H 7/04; H05H 2277/11; A61N 2005/1085–1098; A61N 5/10–1084
See application file for complete search history.

(56) References Cited

U.S. PATENT DOCUMENTS 2,331,788 A 10/1943 Baldwin
4,646,027 A 2/1987 Birx et al.
(Continued)

FOREIGN PATENT DOCUMENTS

KR 1020200038429 4/2020
WO 2019059932 A1 3/2019
WO 2022146855 7/2022

OTHER PUBLICATIONS

A. Fateev, G. Dolbilov, I. Ivanov, V. Kosukhin, N. Lebedev, V. Petrov, V. Razuvakin, V. Shvetsov and M. Yurkov, "Status of the first stage of linear induction accelerator SILUND-21," in Proceedings Particle Accelerator Conference, Dallas, TX USA, 1995.

(Continued)

*Primary Examiner* — Tuan T Lam
(74) *Attorney, Agent, or Firm* — Perkins Coie LLP

(57) ABSTRACT

Methods, devices and systems for ultra-high dose radiotherapy are disclosed. The described techniques rely in-part on active switching control of a photoconductive switch during the time the accelerator is accelerating charged particles to produce the output radiation at the desired dose rates. One radiotherapy system includes a particle accelerator configured to receive charged particles from a pulsed source. The particle accelerator includes a pipe configured to allow the charged particles to pass through as a beam, a magnetic core positioned proximate to the pipe and coupled to the pulsed source, and at least one multilayer insulator positioned adjacent to the pipe and the magnetic core. The system also includes a photoconductive switch coupled to (Continued)

the particle accelerator and configured to supply the particle accelerator with a plurality of voltage pulses.

17 Claims, 11 Drawing Sheets

(51) Int. Cl.
  *H05H 7/04* (2006.01)
  *H05H 7/06* (2006.01)
  *H05H 7/22* (2006.01)
(52) U.S. Cl.
  CPC ............... *H05H 7/06* (2013.01); *H05H 7/22* (2013.01); *A61N 2005/1088* (2013.01); *A61N 2005/1089* (2013.01); *H05H 2277/11* (2013.01)

(56) References Cited

U.S. PATENT DOCUMENTS

| | | | |
|---|---|---|---|
| 4,888,556 | A | 12/1989 | Buttram et al. |
| 6,066,901 | A | 5/2000 | Burkhart et al. |
| 7,710,051 | B2 | 5/2010 | Caporaso et al. |
| 10,270,368 | B2 | 4/2019 | Sampayan |
| 10,282,567 | B2 | 5/2019 | Miller et al. |
| 10,792,517 | B2 | 10/2020 | Lee et al. |
| 11,697,032 | B2* | 7/2023 | Sampayan ............ A61N 5/1067 600/1 |
| 2007/0228301 | A1 | 10/2007 | Nakano |
| 2009/0224700 | A1 | 9/2009 | Chen et al. |
| 2010/0032580 | A1 | 2/2010 | Caporaso et al. |
| 2010/0102246 | A1 | 4/2010 | Park et al. |
| 2011/0101376 | A1* | 5/2011 | Caporaso ................. H05H 7/00 257/77 |
| 2011/0133203 | A1 | 6/2011 | Werne et al. |
| 2013/0140468 | A1 | 6/2013 | Chen |
| 2014/0368108 | A1 | 12/2014 | Nahum et al. |
| 2014/0371511 | A1 | 12/2014 | Zwart et al. |
| 2016/0238412 | A1* | 8/2016 | Germann ............... G01D 5/204 |
| 2016/0287905 | A1 | 10/2016 | Liger |
| 2018/0161595 | A1 | 6/2018 | Fuentes |
| 2022/0203135 | A1 | 6/2022 | Sampayan et al. |
| 2022/0219014 | A1 | 7/2022 | Sampayan et al. |
| 2022/0304136 | A1* | 9/2022 | McNeur ............... A61N 5/1077 |
| 2023/0310897 | A1 | 10/2023 | Sampayan et al. |

OTHER PUBLICATIONS

A. Toepfer, "A review of accelerator concepts for the advanced hydrotest facility," in 19th International Linear Accelerator Conference, Chicago, IL, 1998.
B. Kulke and R. Kihara, "Recent Performance Improvements on Fxr," IEEE Trans. Nucl. Sci., vol. 30, No. 4, pp. 3030-3032, 1983.
C. Karzmark, "Advances is linear accelerator design for radiotherapy," Med. Phys., vol. 11, No. 2, pp. 105-128, 1984.
C. Shang, Y.-J. Chen, G. Caporaso, T. Houck, N. Molau, S. Nelson, W. Ng and J. Fockler, "BBU design of linear induction accelerator cells for radiography application," in 1997 Particle Accelerator Conference, Vancouver, BC Canada, 1997.
D. Birx, "Induction linear accelerators," AIP Conference Proceedings, vol. 249, pp. 1553-1614, 1992.
E. Ginzton, W. Hansen and W. Kennedy, "A linear electron accelerator, " Rev. Sc. Instr., vol. 19, pp. 89-108, 1948.
E. Merle, R. Boivinet, M. Mouillet, O. Pierret, P. Anthouard, J. Bardy, C. Bonnafond, A. Devin, P. Eyl and C. Vermare, "Installation of the AIRIX Induction Accelerator, " in 19th International Linear Accelerator Conference, Chicago, IL USA, 1998.
E. Schuler, et al., "Experimental Platform for Ultra-high Dose Rate FLASH Irradiation of Small Animals Using a Clinical Linear Accelerator," Int J of Rad Oncology Biol Phys, vol. 97, No. 1, pp. 195-203, 2017.

G. Becker and D. Caswell, "Operation of a six-MeV linear accelerator," Rev. Sci. Instr., vol. 22, No. 6, pp. 402-405, 1951.
G. Caporaso, et al., "A compact linac for intensity modulated proton therapy based on a dielectric wall accelerator," Physica Medica, vol. 24, No. 2, pp. 98-101, 2008.
G. R. Neil, J. Edighoffer, P. Livingston, J. Rawls and I. Smith, "The induction-FEL design for the White Sands missile range," Nucl. Instr. Meth. Phys. Res. A, vol. 296, No. 1-3, pp. 257-262, 1990.
H. Kirbie, B. Hickman, B. Lee, C. Ollis, C. Brooksby and R. Saethre, "An all solid state pulse power source for high PRF induction accelerators," in 23rd International Power Modulator Symposium, Rancho Mirage, CA USA, 1998.
H. Kirbie, G. Caporaso, D. Goerz, R. Hanks, B. Hickman, B. Lee, C. Brooksby and R. Saethre, "MHz repetition rate solid-state driver for high current induction accelerators," in 1999 Particle Accelerator Conference, New York, NY USA, 1999.
I. Smith, "Induction voltage adders and the induction accelerator family, " Phys. Rev. ST Accel. Beams, vol. 7, pp. 064801-1-40, 2004.
I. Uetomi, M. Yamazaki, H. Kobayashi and I. Sato, "Extended Theory of Beam Loading in Electron Linac," Jpn. J. Appl. Phys., vol. 32, No. 6A, pp. 2858-2864, 1993.
International Search Report and Written Opinion for International Patent Application No. PCT/US2022/012288 mailed May 4, 2022 (10 pages).
J. A. Watson, A. N. Payne, S. E. Sampayan and C. W. Ollis, "Precision voltage regulation on the 5 KHz, 3.125 MW ETA-II pulsed power system," in Eighth IEEE International Conference on Pulsed Power, San Diego, CA, USA, 1991.
J. Barnard, R. Bangerter, A. Faltens, T. Fessenden, A. Friedman, E. Lee, B. Logan, S. Lund, W. Meier, W. Sharp and S. Yu,, "Induction accelerator architectures for heavy-ion fusion," Nucl. Instr. Meth. in Phys. Res. A, vol. 415, No. 1-2, pp. 218-228, 1998.
J. Beal, N. Christofilos and R. Hester, "The Astron Linear Accelerator," IEEE Trans. Nucl. Sci., vol. 16, No. 3, pp. 294-298, 1969.
J. Bourhis, et al., "Treatment of a first patient with FLASH-radiotherapy," Radiotherapy and Oncology, vol. 139, pp. 18-22, 2019.
J. D. Wilson, E. M. Hammond , G. S. Higgins and K. Petersson, "Ultra-High Dose Rate (FLASH) Radiotherapy: Silver Bullet or Fool's Gold?, " Front. Oncology, vol. 9, p. 1563, 2020.
J. Deng, B. Ding, J. Shi, Y. He, J. Li, Q. Li, G. Cao, L. Wen and G. Dai, "Upgrading of Linear Induction Accelerator X-Ray Facility (LIAXF), " in 19th International Linear Accelerator Conference, Chicago, Il USA, 1998.
J. Deng, et al., "Design of the DRAGON-I Linear Induction Accelerator, " in 21st International Linear Accelerator Conference, Gyeongju, Korea, 2002.
J. Melton and E. Rose, "A model for the magnetic cores of linear induction accelerator cells," in Tenth IEEE International Pulsed Power Conference, Albuquerque, NM USA, 1995.
J. Smith, V. Bailey, H. Lackner and S. Putnam, "Performance of the spiral line induction accelerator," in Proceedings of the 1997 Particle Accelerator Conference, Vancouver, BC Canada, 1997.
J. Weir, J. Boyd, Y.-J. Chen, J. Clark, D. Lager and A. Paul, "Improved ETA-II accelerator performance," in Proceedings of the 1999 Particle Accelerator Conference, New York, NY USA, 1999.
K. Brown, "Properties of iris-loaded guides, " in Conference on Linear Accelerators, Upton, NY, 1961.
K. Sampayan and S. Sampayan, "Wide Bandgap Photoconductive Switches Driven by Laser Diodes as a High-Voltage Mosfet Replacement for Bioelectrics and Accelerator Applications," in IEEE Pulsed Power & Plasma Science, Orlando, FL USA, 2019.
K. Takayama and R. J. Briggs, Induction Accelerators, New York: Springer, 2011.
K. Yatsui, et al., "Pulse-power technology and its applications at LBT, Nagaoka," in 11th International Conference on High-Power Particle Beams, Prague, Czech Republic, 1996.
L. Reginato, "The Advanced Test Accelerator (ATA), a 50-MeV 10-KA Induction Linac, " IEEE Trans. Nucl. Sci., vol. 30, pp. 2970-2974, 1983.

(56) References Cited

OTHER PUBLICATIONS

L. Yang, L. Yang, F. Yang and X. Ma, "Slow-Scale and Fast-Scale instabilities in parallel-connected single-phase H-bridge inverters: A design-oriented study," Int. J. Bifurcation and Chaos, vol. 30, No. 1, pp. 2050005-1-20, 2020.

M. Burns, et al., "DAHRT accelerators update and plans for initial operation, " in Particle Accelerator Conference, New York, NY USA, 1999.

M. Burns, et al., "Status of the DARHT phase 2 long-pulse accelerator, " in 2001 Particle Accelerator Conference, Chicago, IL USA, 2001.

M. Hodgdon, "Mathematical theory and calculations of magnetic hysteresis curves, " IEEE Trans. Magnetics, vol. 24, No. 6, pp. 3120-3122, 1988.

M. Jaccard, et al., "High dose-per-pulse electron beam dosimetry: Commissioning of the Oriatron eRT6 prototype linear accelerator for preclinical use," Med. phys., vol. 45, No. 2, p. 863-874, 2018.

M.-C. Vozenin, et al., "The Advantage of FLASH Radiotherapy Confirmed in Mini-pig and Cat-cancer Patients, " Clin Cancer Res, vol. 25, No. 1, pp. 35-42, 2019.

N. Christofilos, R. Hester, W. Lamb, D. Reagan, W. Sherwood and R. Wright, "High current linear induction accelerator for electrons," Rev. Sci. Instr., vol. 35, No. 7, pp. 886-890, 1964.

N. Khizhnyak, V. Tolok, V. Chechkin and N. Nazarov, "The acceleration of large current pulses in electron linear accelerators," Plasma Physics (J. Nucl. Ener. C), vol. 4, pp. 129-134, 1962.

O. Zlobinskaya, et al., "The Effects of Ultra-High Dose Rate Proton Irradiation on Growth Delay in the Treatment of Human Tumor Xenografts in Nude Mice," Radiat. Res., vol. 181, No. 2, pp. 177-183, 2014.

P. Anthouard, et al., "Airix at CESTA," in 11th International Conference on High-Power Particle Beams, Prague, Czech Republic, 1996.

P. Corcoran, et al., "Experimental tests of the power supply and prototype cell for the 1.5 MeV SLIA acceleration unit," in 1991 IEEE Particle Accelerator Conference, San Francisco, CA USA, 1991.

P. G. Maxim, P. Keall and J. Cai, "Point/Counterpoint, FLASH radiotherapy: Newsflash or flash in the pan?," Med. Phys., vol. 46, No. 10, pp. 4287-4290, 2019.

P. Montay-Gruel, et al., "Irradiation in a flash: Unique sparing of memory in mice after whole brain irradiation with dose rates above 100 Gy/s," Radiotherapy and Oncology, vol. 124, No. 3, pp. 365-369, 2017.

P. Seidl, et al., "Irradiation of materials with short, intense ion pulses at NDCX-II," Laser and Part. Beams, vol. 35, No. 2, pp. 373-378, 2017.

R. Cassel, M. Nguyen, E. Cook and C. Brooksby, "A hybrid solid state induction modulator for klystrons, " in 16th IEEE International Pulsed Power Conference, Albuquerque, NM USA, 2007.

R. J. Adler, "Pulse Power Formulary," Air Force Office of Scientific Research, Washington, DC USA, 1989.

R. Neal, "Design of linear electron accelerators with beam loading," J. Appl. Phys., vol. 26, No. 7, pp. 1019-1024, 1958.

R. Post and N. Shiren, "The Stanford Mark II Inear accelerator," Rev. Sci. Instr., vol. 26, No. 2, pp. 205-209, 1955.

R. Wideröe, "Über ein neues Prinzip zur Herstellung hoher Spannungen," Archiv für Elektrotechnik, vol. 21, No. 4, p. 387-406, 1928.

S. Allen, et al., "Generation of high power 140 GHz microwaves with an FEL for the MTX experiment," in Proceedings of International Conference on Particle Accelerators, Washington, DC USA, 1993.

S. Benedetti, A. Grudiev and A. Latina, "High gradient linac for proton therapy," Physical Rev. Accel. Beams, vol. 20, pp. 040101-1-19, 2017.

S. Mazumder, "Stability analysis of parallel DC-DC converters," IEEE Trans. Aerospace Electr. Syst., vol. 42, No. 1, pp. 50-69, 2006.

S. Sampayan, et al., "Characterization of carrier behavior in photonically excited 6H silicon carbide exhibiting fast, high voltage, bulk transconductance properties," Scientific Reports, 2021.

S. Sampayan, et al., "Performance characteristics of an induction linac magnetic pulse compression modulator at multi-kilohertz pulse repetition frequencies," in IEEE Particle Accelerator Conference, San Francisco, CA USA, 1991.

S. Sampayan, G. Caporaso, Y.-J. Chen, D. Decker and W. Turner, "Energy sweep compensation of induction accelerators," in 1990 LINAC Conference, Albuquerque, NM USA, 1990.

S. Sampayan, P. Vitello, M. Krogh and J. Elizondo, "Multilayer high gradient insulator technology," IEEE Trans. Dielect. Elect. Insul., vol. 7, No. 3, pp. 334-339, 2000.

T. Feder, "High radiation dose rates may improve cancer therapy," Physics today, vol. 73, No. 12, pp. 24-26, 2020.

T. Houck, et al., "Measured and theoretical characterization of the RF properties of stacked, high-gradient insulator material," in Proceedings of the 1997 Particle Accelerator Conference, Vancouver, BC Canada, 1997.

T. Mackie, T. Holmes, S. Swerdloff, P. Reckwerdt, J. Deasy, J. Yang, B. Paliwal and T. Kinsella, "Tomotherapy: A new concept for the delivery of dynamic conformal radiotherapy," Med. Phys., vol. 20, pp. 1709-1719, May 31, 1993.

V. Smirnov and S. Vorozhtsov, "Modern compact accelerators of cyclotron type for medical applications," Phys. Part. Nuclei, vol. 47, p. 863-883, 2016.

W. Panofsky and M. Bander, "Asymptotic theory of beam break-up in linear accelerators," Re. Sci. Instr., vol. 39, No. 2, pp. 206-212, 1968.

W. Turner, G. Caporaso, G. Craig, J. DeFord, L. Reginato, S. Sampayan, R. Kuenning and I. Smith, "Impedance characteristics of induction accelerator cells," in International Conference on High-Power Particle Beams, Karlsruhe, Germany, 1988.

W. Waldron, et al., "The NDCX-II engineering design," Nucl. Instr. Meth. Phys. Res. A, vol. 733, pp. 226-232, 2014.

W. Waldron, J. Galvin, W. Ghiorso and C. Pappas, "The design and testing of an inductive voltage adder for ALS-U kicker magnets," in IEEE International Power Modulator and High Voltage Conference, San Francisco, CA USA, 2016.

Y.-J. Chen, et al., "Compact Dielectric Wall Accelerator Development For Intensity Modulated Proton Therapy and Homeland Security Applications," in 10th International Conference on Applications of Nuclear Techniques, Crete, Greece, 2009.

International Search Report and Written Opinion mailed Jun. 2, 2022 for International Patent Application No. PCT/US2021/065016.

Maxim, P., G., et al., "PHASER: A platform for clinical translation of FLASH cancer radiotherapy," Radiotherapy and Oncology 139 (2019) 28-33, Elsevier, 6 pages.

S. Humphries, Principals of Charged Particle Acceleration, Hoboken, NJ: John Wiley and Sons, 1999.

S. Sampayan, P. Vitello, M. Krogh and J. Elizondo, "Multilayer ultra-high gradient insulator technology," in 18th International Symposium on Discharges and Electrical Insulation in Vacuum, Eindhoven, Netherlands, 1998.

Extended European Search Report of European Patent Application No. 21916267.4 dated Jun. 4, 2024 (8 pages).

Schuller et al. "The European Joint Research Project UHDpulse—Metrology for advanced radiotherapy using particle beams with ultra-high pulse dose rates," Physica Medica, Acta Medica Edizioni E Congressi, Rome IT, Nov. 9, 2020, 80:134-150.

* cited by examiner receiving, at a particle accelerator of a particle accelerator system, a beam of charged particles from a particle source
1002 producing a plurality of voltage pulses by the photoconductive switch in response to receiving light that is incident on the doped crystalline material
1004 accelerating the beam of charged particles by the particle accelerator based on the plurality of voltage pulses to produce one or more output radiation beams for flash radiotherapy
1006

FIG. 10

FLASH RADIOTHERAPY ACCELERATOR SYSTEM

CROSS-REFERENCE TO RELATED APPLICATIONS

This patent document claims priority to and benefits of U.S. Provisional Patent Application No. 63/136,645 entitled "LINEAR INDUCTION ACCELERATORS AS INTENSE FLASH RADIOTHERAPY SOURCES," filed on Jan. 13, 2021. The entire contents of the before-mentioned patent applications are incorporated by reference as part of the disclosure of this patent document.

STATEMENT REGARDING FEDERALLY SPONSORED RESEARCH OR DEVELOPMENT

This invention was made with Government support under Contract No. DE-AC52-07NA27344 awarded by the United States Department of Energy, under Contract No. DE-AR0000907 awarded by the Advanced Research Projects Agency-Energy (ARPA-E), under Grant No. 1519964 by the National Science Foundation, and under Grant No. 17-01-03 by the State of California CalSEED Program. The Government has certain rights in the invention.

TECHNICAL FIELD

This document relates to FLASH radiotherapy systems and in particular to FLASH radiotherapy systems that use a charged particle accelerator.

BACKGROUND

Recent studies indicate that intense pulsed radiation at high dose rates for cancer therapy has better efficacy and is less damaging to healthy tissue than lower radiation dose given over a longer period of time. This approach involves ultra-high dose rate radiotherapy and is sometimes referred to as "FLASH" radiotherapy. Although the mechanisms are not clearly understood, FLASH radiotherapy is hypothesized to provide better efficacy due to hypoxic effects. The response of tumors appears to be independent of dose rate but healthy tissue seems to gain protection from radiation damage by the reduced production of free radicals during a momentary high dose rate pulse. Research to date indicates these protective effects within healthy tissue become even more pronounced at dose rates above 100 Grays per second (Gy/s). This technique requires controlling not only the total dose, but also the dose rate. Therefore, there is a need to control and deliver such radiotherapy dose rate.

SUMMARY

The disclosed embodiments relate to methods, devices and systems that address the shortcomings of the existing radiotherapy systems and, among other features and benefits, enable FLASH radiotherapy via delivery of radiation with high dose rates in a controllable fashion using an accelerator. The disclosed techniques rely in-part on active switching control during the time the accelerator is accelerating charged particles to produce the radiation.

One aspect of the disclosed embodiments relates to a FLASH radiotherapy system that includes a particle accelerator configured to receive charged particles from a pulsed source. The particle accelerator includes a pipe configured to allow the charged particles to pass through as a beam, a magnetic core positioned proximate to the pipe and coupled to the pulsed source, and a multilayer insulator positioned adjacent to the pipe and the magnetic core. The system also includes a photoconductive switch coupled to the particle accelerator and configured to supply the particle accelerator with a plurality of voltage pulses. The particle accelerator is operable to accelerate the charged particles based on the plurality of voltage pulses, and to produce an output beam comprising one or more radiation pulses for radiotherapy.

BRIEF DESCRIPTION OF THE DRAWINGS

FIG. 10 illustrates a set of example operations that can be carried out to produce an output radiation beam in a radiotherapy system in accordance with one or more embodiments of the present technology.

DETAILED DESCRIPTION

Figure 1:
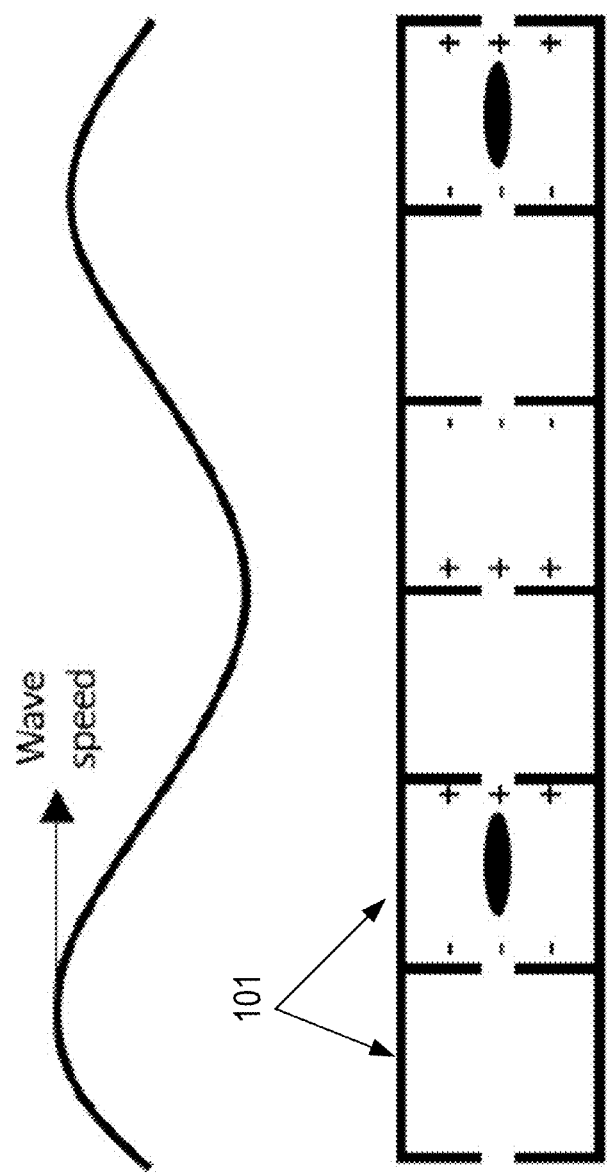
FIG. 1 is a schematic diagram illustrating example acceleration of electrons in a traveling wave linear accelerator.

Much of the work in FLASH radiotherapy to date uses modified microwave driven linear accelerators, also referred to as Hansen type microwave driven linear accelerators. As shown in FIG. 1, the modified microwave driven linear accelerators use longitudinal resonance of a sinusoidally varying electromagnetic field in parallel with the electron motion. Electrons in resonance experience a net positive accelerating gradient along the full length of the accelerator. The operating frequency is typically 3-GHz. The free-space propagation speed of an electromagnetic wave is slightly faster than relativistic electrons. To match the speeds, microwave energy is injected into an iris loaded "slow wave" structure. In this structure, the electromagnetic wave is in resonance with the individual cavities 101 and the iris aperture determines the relative phase shift cavity to cavity. By matching the electromagnetic wave speed to that of the electrons, energy is transferred. In practice, this type of accelerator is well suited for particles such as electrons that can be accelerated to near the speed of light in a fairly short distance. Because of the simplicity and compactness of the approach, the iris loaded linear accelerator and its variations are dominant in the radiotherapy field.

Acceleration gradients can be greater than 10-MV/m which is limited by internal breakdown and power. Typical requirements are 0.4-MW/MeV of accelerator energy. For a fixed gradient, power scales as the square root of the natural logarithm of the iris aperture radius. Because of the high-power requirement, these systems operate at a low duty cycle, typically less than 0.1%. In this format, the macro pulses are typically a few microseconds in length and at a rate of 100-300 pulses per second. The structure also requires a microwave fill time for each macro pulse of approximately 1-μs (for ~400-mA of beam current) before the electrons can be accelerated. Thus, the format for electron beam delivery is ~10 s of picosecond micro pulses delivered in a macro microsecond burst, at a rate of 100-300 bursts per second.

To increase the dose rate in such iris loaded structures, the beam current can be increased. One of the additional characteristics of this type of accelerator is that the structure is optimized for a given beam current, making an efficient design essentially single current point. Higher currents can be designed for, but they negatively affect the phase velocity of the electromagnetic wave so that the resonance with electron longitudinal motion is spoiled. This effect sets practical limits to ampere level beams in these traveling wave structures. Furthermore, other oscillatory modes are excited in the structure by the beam itself. These electromagnetic modes are asymmetric and can impart a transverse motion to the beam causing wall impact, leading to shortening of the beam pulse. Known as a transverse or beam break-up instability, the exponential growth of this effect scales as the square-root of the beam current divided by the radius of the cavity. This scaling requires higher currents to be compensated by larger cavities to suppress the instability. Large cavities, however, require higher power and so optimization between the two is required.

While there are many different manifestations of resonance acceleration techniques, the fundamental concept is to overcome the limitations of single stage acceleration techniques. High gradient linear accelerators continue to be more a subject of study for medical applications.

Linear Induction Accelerator Technology

Figure 2A:
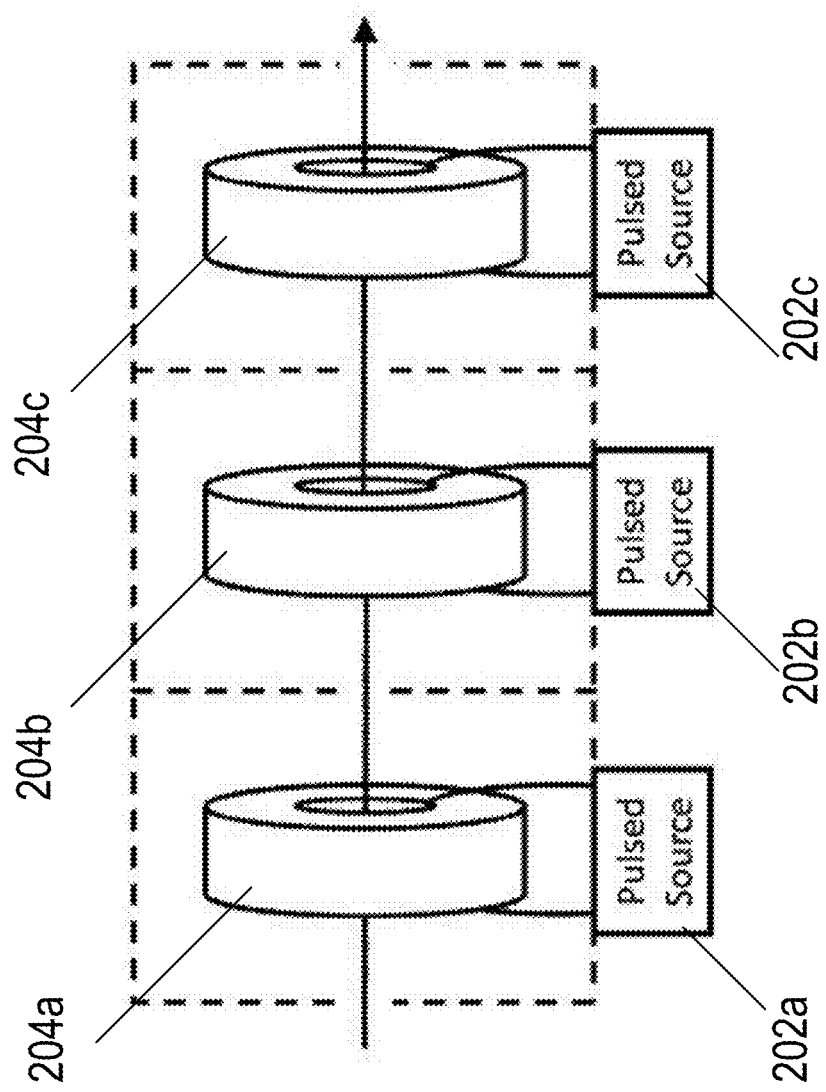
FIG. 2A is a schematic diagram illustrating example acceleration of electrons with a linear induction accelerator (LIA).
Figure 2B:
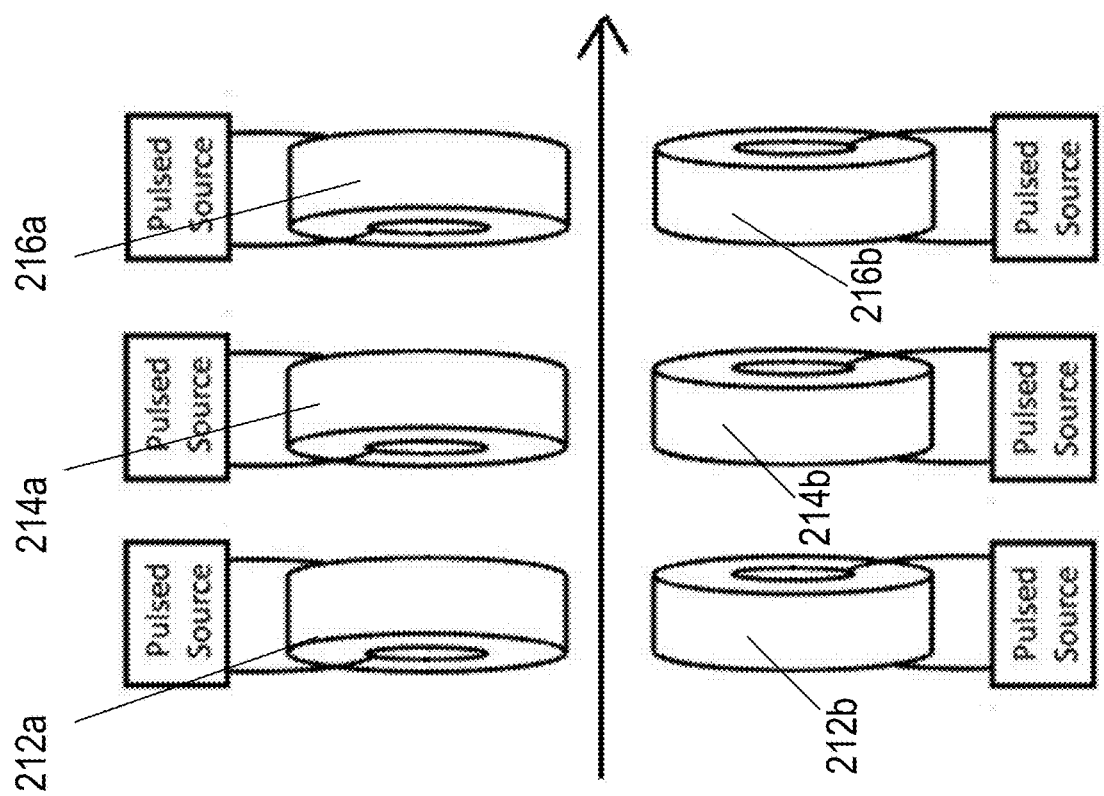
FIG. 2B is a schematic diagram illustrating another example acceleration of electrons with a linear induction accelerator (LIA).

One non-resonance acceleration method is the linear induction accelerator (LIA), a high dose rate system developed to overcome the beam current limitations in standard microwave linear accelerators. FIG. 2A is a schematic diagram illustrating example acceleration of electrons with a linear induction accelerator (LIA). As shown in FIG. 2A, pulsed sources 202a, 202b, 202c are applied to three corresponding magnetic cores 204a, 204b, 204c, and the path of the charged particle beam is illustrated by the arrow through the center of the cores. FIG. 2B illustrates another example in which two sets of magnetic cores 212a, 214a, 216a and 212b, 214b, 216b are coupled to corresponding pulsed sources. For example, a first magnetic core 212a is positioned close to the charged particle beam pipe (e.g., at one side) and a second magnetic core 212b is also positioned close to the charged particle beam pipe (e.g., at the opposite side). When a pulse is applied to a winding around the core, a longitudinal electric field is generated that accelerates the charged particles in the pipe. This electric field is maintained for the pulse duration so long as the magnetic core does not saturate (e.g., the point at which leakage current around the core increases, and the field collapses). This saturation effect is based on the core material, the cross-sectional area, and the volt-second product of the applied pulse. To return the core back to the original magnetic state after the acceleration pulse, a small voltage opposite to the applied pulse is maintained across each cavity. Although not considered a resonant acceleration method, proper synchronization of the individual pulsed sources is required to accelerate the charged particle beam. It is noted that while FIGS. 2A-B illustrate techniques using magnetic cores, other means are available for the construction of an LIA.

While originally developed as an intense electron source, this acceleration method is completely species independent so long as the pulsed sources are properly synchronized, and the beam dynamics are properly managed. The same induction accelerator cavity can be used for either electron or ion acceleration, particularly if high gradient multilayer insulator technology, which shows no polarity effect, is used. More recent experiments have demonstrated high dose-rate ion beams (2-A $He^+$, 2.4-ns pulse, and a 1-mm radius spot) for heavy ion fusion. In this particular system, conversion for $He^+$ mainly required increasing the magnetic field of the integral solenoid magnets to accommodate the increased space charge of the ion beam.

One of the key features of this type of accelerator system is that the beam pipe radius can be arbitrary and has little effect on the acceleration gradient. This feature has also led to acceleration of multiple ion beamlets through a single accelerator cavity or multiple separate passes through large aperture cavities in a recirculating electron accelerator system. For electrons, the exponential growth rate of the beam breakup instability in an LIA scales as the current divided by the beam pipe radius squared. Since the gradient and pulsed source requirement are independent of the beam pipe radius, the dimension becomes a free parameter in suppression of the instability. Also, because the acceleration process is non-resonant with the cavity, internal features can be optimized to suppress the instability growth. Finally, using the multilayer insulator structure in the acceleration gap has the added property of suppressing the transverse resonances in the cavity.

Power loss in an LIA is mainly attributed to the leakage current around the core and is a function of the magnetic material. For instance, NiZn ferrites used in modern accelerators behave more like a high impedance load (~200-ohm) during most of the applied pulse. For beam currents below 100-A, that impedance dominates. As a result, the beam current can be adjusted over a wide range without perturbing the match between the pulsed source and cavity. For extremely high-power beams (~kA), efficiencies can exceed 80% for smaller magnetic core radius but likewise need to be traded against growth of transverse instabilities.

One of the main drawbacks of the LIA is the gradient. Older machines were typically <0.5-MV/m. Gradient scales as the inverse of the pulse width. Thus, achieving high gradients requires minimizing the pulse width and achieving fast rise and fall time switching to maximize the region of the pulse where the electrons are accelerated. One accelerator that can achieve over 0.5 MeV is the Experimental Test Accelerator-II (ETA-II). The pulsed sources utilized a two-stage thyratron system driving a Melville line. The Melville line is a series network of capacitor-non-linear inductor-capacitor elements that compress the energy in time to deliver high peak power. At full voltage operation, the system can deliver 135-kV into a 2-ohm load at 5,000-Hz at better than 90% efficiency. In this particular system, one pulsed source drove twenty accelerator cavities. ETA-II was originally built as a precision electron beam source. Component development enabled it to deliver an approximately 3,000-A electron beam at 6.5-MeV in a 50-ns pulse at a 5,000-Hz repetition rate. To use the architecture for a 170 MeV electron accelerator, the accelerator was required to provide an ultra-stable electron beam with sub-mm motion and spot size. To provide this precision, beam stability and control and energy regulation was stringent within the pulse (<1%) and also pulse-to-pulse (<0.1%). Because of the precision beams ETA-II provided, it also served as the baseline architecture for modern short pulse dynamic radiograph accelerators. Later, the system was used as a test bed for bremsstrahlung target experiments and downstream beamline component development for the DARHT-II dynamic radiography FLASH x-ray system. Table 1 shows several other accelerators with energies greater than 5-MeV.

| Facility | Energy (MeV) | Beam Current (A) | Pulse Width (ns) | Maximum Pulse Repetition Rate (Hz) |
|---|---|---|---|---|
| SLIA | 5.5 | 10,000 | 30 | |
| Astron | 6 | 800 | 300 | 1400 |
| ETA-II | 6.5 | 3,000 | 50 | 5000 |
| ETIGO-III | 8 | 5,000 | 30 | 1 |
| PIVAR | 8 | 3,500 | 80 | 1 |
| SILUND-21 | 10 | 1,000 | 60 | |
| LIAXF/LIAXFU | 12 | 2,600 | 90 | 1 |
| FXR | 17 | 3,000 | 60 | 0.3 |
| DARHT-II | 17 | 2,100 | 1,600 | 1 |
| DARHT-I | 20 | 2,000 | 60 | 1 |
| AIRIX | 20 | 4,000 | 80 | 1 |
| DRAGON-I | 20 | 3,000 | 90 | 1 |
| LIA 30/250 | 30 | 250 | 500 | 50 |
| ATA | 45 | 10,000 | 75 | 1000 |

Figure 3:
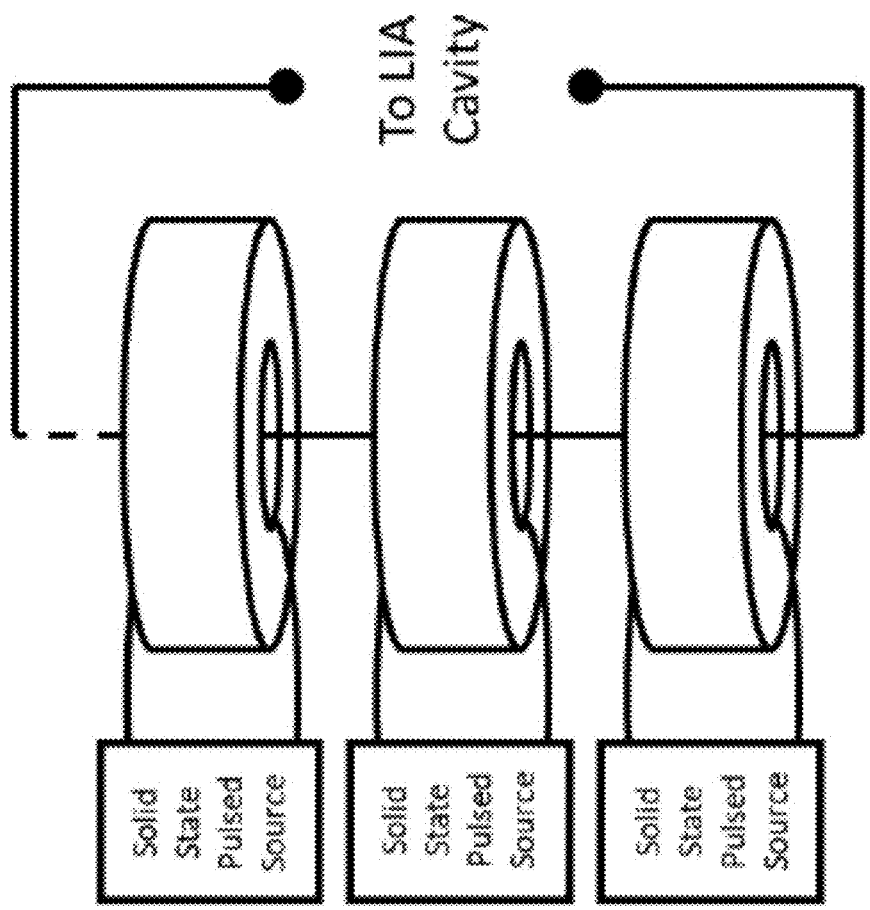
FIG. 3 is a schematic diagram illustrating a solid-state technology using distributed magnetic core and an adder stalk to achieve high voltages.

Pulsed Source Development s pulsed source technology is antiquated. With the introduction of solid-state power electronic devices driven by need in the electric power industry, the pulsed source drive for induction accelerators has become more simplified, agile, and compact over the last two decades. As shown in FIG. 3, a solid-state pulsed source approach differing from the ETA-II system was designed around field effect transistors (FETs) and insulated gate bipolar transistors (IGBTs). The solid-state pulsed source approach was able to deliver 15-kV into about 3-ohms with a flexible pulse width from 200-ns to 1.5-µs at a pulse repetition frequency up to 1 MHz, and was quickly scaled up to 45-kV at 2 MHz. Achieving these rates in an LIA required that, after providing the main acceleration pulse, the same pulsed source provided a lower, opposite polarity pulsed voltage to the accelerator cavity. This opposite polarity pulse had the same volt-second product as the main pulse and would restore the magnetic state of the cores for the next acceleration pulse.

As power electronics mature, these systems can be adapted to use wide bandgap semiconductors. An example of such a system is a high-power klystron driver. In a high-power klystron driver system, a group of pulsed source modules referenced to ground potential are stacked in series. The output of each of the pulsed sources threads a single magnetic core forming an LIA like "adder." Rather than a charged particle beam threading each core, a single conductor (sometimes referred to as an "adder stalk") threads all the cores. Absent any losses, this conductor develops a potential equal to the sum of each pulsed source output. The elegance of this approach is that the parasitic elements that usually accompany most high voltage step-up methods are minimized. As a result, the pulse fidelity from each of the single sources is closely maintained in the summed output.

This seemingly complex approach to the pulsed sources results from the fundamental limitation of junction devices. For a particular solid-state device to hold off high voltage, the thickness needs to be adequate enough to remain below the critical electric field, $E_c$. This field is the point at which charged carriers in the crystal lattice begin to avalanche. As a result, this thicker structure results in longer transit times for the carriers and thus longer turn-on times. Even in materials having high $E_c$ such as SiC, turn-on times for a 15-kV device can be a large fraction of a microsecond. This slow turn-on for the 15-kV device is inadequate for LIA pulsed source technology.

Another disadvantage of the adder approach is that oscillations along the stalk can be excited. These oscillations combine with the applied pulse to cause unwanted beam control and stability issues. Further, because of the relatively tight magnetic coupling between pulsed source modules though the adder stalk, the close proximity of each pulsed source to the adjoining sources, and parasitic coupling from the control and power system wiring, the overall topology becomes analogous to a distributed power system using switched converters. Unwanted chaotic behavior can occur resulting in unwanted and hard to predict sporadic oscillations.

Photoconductive Switch—Optical Transconductance Varistor (OTV)

Beam energy determines the penetration depth. Controlling dose rate for a given penetration depth requires maintaining constant energy while controlling the current either injected into the accelerator by the particle generator or within the accelerator itself. To control total dose for the specified dose-rate, the temporal character of the individual pulse or pulses which accelerate the charged particle needs to be controlled. Conversely, if time shape of the applied pulse is the controlling parameter used to control dose in a pulsed machine driven by high voltage pulse sources, beam current can be increased or decreased as necessary for the given treatment time. All these approaches require control of an active switch.

The active switch utilized to discharge voltage across a vacuum gap is an enabling component of an accelerator system in accordance with the disclosed embodiments. It must reliably hold off high voltage until the voltage is required across the acceleration gap, turn on precisely when required, allow a controlled flow of current (typically 10's to many 100's of amps) for the desired time and turn off consistently within 10's of nanoseconds from command to turn off when required. This sequence must be performed repeatedly at a required rate for a specified number of times in order for the total required dose to be delivered. In addition, the switch needs to be able to be infinitely variable in the on-state conditions so as to precisely control the dose rate output of the accelerator. For pulse control, desired characteristics of the switching device include variable pulse time length; turn on and turn off times much shorter than the pulse time; switching control unaffected by the high voltage action; long lifetime and simplicity of use. While such a capability may be achievable at low voltages with transistors and MOSFETS, demands for accomplishing this demanding application at voltages necessary for a pulsed power accelerator (approximately 10's to 100's of kilovolts) are extremely unique. Because of this unique requirement, such a switch has not been implemented in a pulsed power accelerator, and existing systems that use inductive coupling or discharge gas switches do not fulfill all the switching requirements, are overly complex and are thus undesirable.

According to an embodiment of the disclosed technology, a photoconductive switch device can be used to address the problems of using FETs or IGBTs mentioned above. Such a switch is an electrical device that operates based on the optical conductivity of a material in response to light. That is, the electrical conductance of the switch is increased as a consequence of irradiation with light. Photoconductive devices are more capable of handling high voltages than junction devices due in part to bulk conduction. Bulk conduction is the process where close to the entirety of the device is turned on simultaneously. In some embodiments, a photoconductive charge trapping apparatus is used as the active switching device because of its high voltage and high pulsed current capability in a compact package. For example, a photoconductive switch device can be used to receive light emitted from a light source via a crystalline material (e.g., comprising silicon carbide). In particular, the crystalline material is doped with a dopant (e.g., vanadium, nitrogen, aluminum, or boron) that forms a mid-gap state within a bandgap of the crystalline material to control a recombination time of the crystalline material so that the crystalline material is configured to exhibit a substantially linear transconductance in response to the light from the light source. The switch can also include electrodes (e.g., two electrodes) coupled to the crystalline material to provide electrical contacts for the crystalline material. The electrodes are configured to establish an electric field across the crystalline material. It should be noted, however, that other types of switches that satisfy the above noted criteria can also be used.

Because the photoconductive active switching devices are very agile, adjusting the beam current, final energy, or temporal behavior can be implemented to produce the desired characteristics. Current produced by the radiation source can be controlled by a grid system in the source of charged particles, e.g., an injector or particle generator. As an alternative, by changing the potentials within the injector, beam current can also be controlled. Further, to control the particle energy, the voltage at the vacuum gap can likewise be controlled. By controlling the temporal character of the applied voltages to either the grid or vacuum gap, the dose rate can then be controlled.

In some embodiments, the high voltage switch and control device is referred to as an optical transconductance varistor (OTV). As discussed above, the OTV relies on bulk conduction where carriers are simultaneously generated throughout the volume using a photoexcitation process. As a result, carrier transit time effects present in conventional power electronic devices are eliminated. By using laser diodes as the excitation source and total internal reflection to increase optical efficiency, it operates analogous to a standard high voltage MOSFET, but at 10's of kV with faster turn on and higher forward power gain. Another capability of OTV is optical isolation and control. Optical isolation eliminates parasitic coupling to the control side and enables isolated series stacking. Thus, to achieve the required voltage for the cavities, a parallel charging-series output switching configuration can be used. Because the output is reduced to a single current loop without the adder stalk, both stalk oscillations and chaotic behavior can be suppressed.

Figure 4:
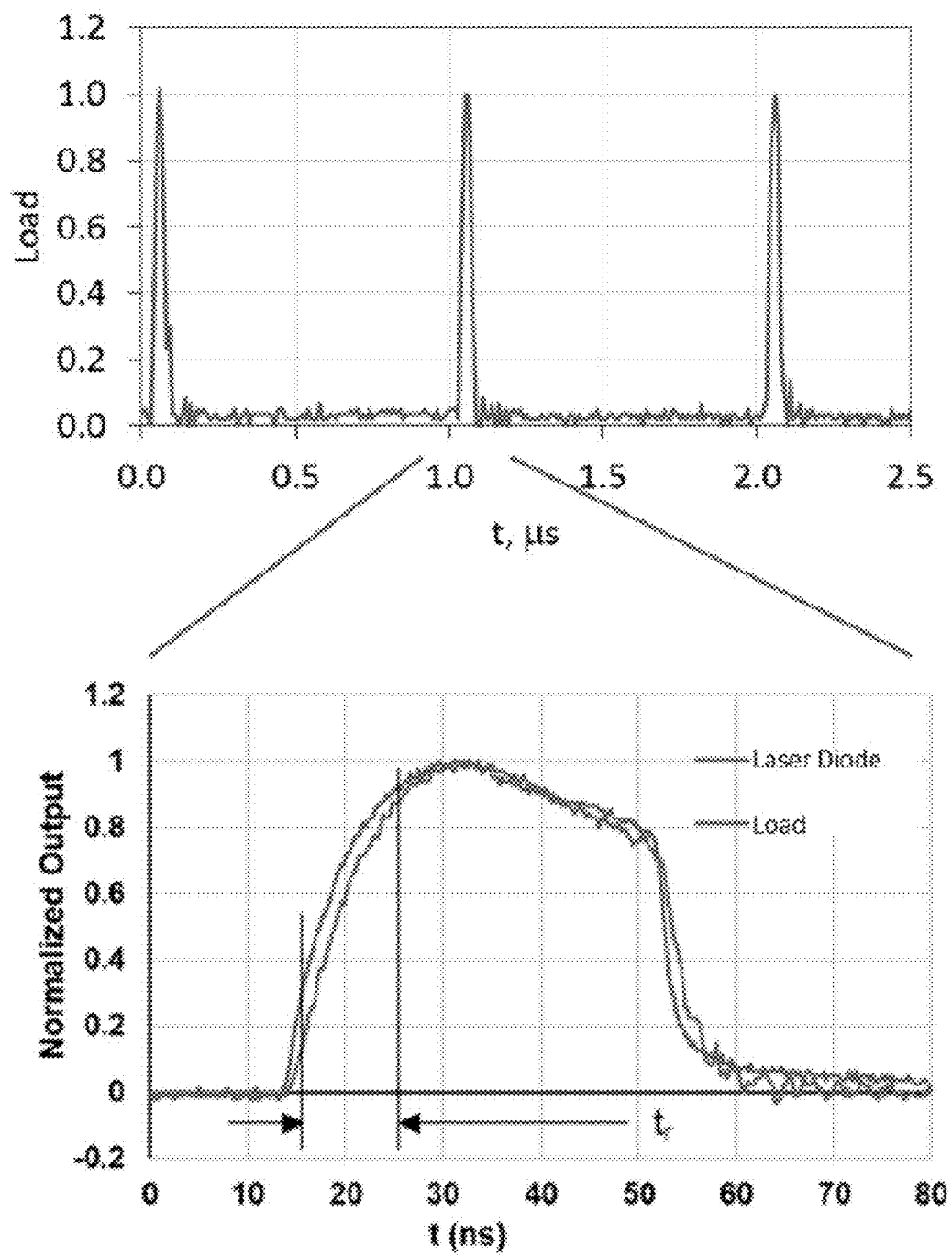
FIG. 4 illustrates example output of an optical transconductance varistor (OTV) system during a lower voltage test for other applications.

Experimentation with the OTV has demonstrated reliable operation to over 20-kV with a stand-off capability to over 30-kV. FIG. 4 illustrates example output of an OTV system during a lower voltage test for other applications. This system operated at 1-MHz pulse repetition frequency. Risetime and pulse shape was limited by the laser diode driver. In this particular data, risetime was about 10-12 ns with a usable pulse width of 25 ns. To operate with an LIA cavity at 120-kv, six of these devices can be organized in series.

Point Design Accelerator Comparison

As explained earlier, FLASH radiotherapy is administered with a sequence of short pulses over a short period of time. The most recent literature requires that for healthy tissue to be spared during irradiation, five conditions or requirements must be fulfilled.

The first is that the instantaneous dose rate (dose within a single pulse) exceed $1.8 \times 10^5$ Gy/s. The second is that the irradiation time to administer the required total dose must be less than 200 ms. Third, as the full radiation dose is typically 8-20 Gy, the average dose rate during the 200 ms period must be above 40 Gy/s and preferably greater than 100 Gy/s. Fourth, the entirety of the irradiated region must be above both the instantaneous and average dose rates. As such narrow beams with Gaussian or similar intensity profiles cannot fulfill this requirement without damaging the surrounding healthy cells. And finally, for the system to be useful for therapy in a clinic setting, the system needs to be less than 100 $m^3$. And of course, because the radiation during this short period must be monitored and controlled very precisely for the patient's long-term health, a means which can both monitor and control the administered dose on these very short, intense, and demanding time scales must be implemented. Meeting all these requirements simultaneously is clearly quite demanding and has not been met to date despite numerous research and development efforts and large sums of money invested to develop such products.

Figure 5:
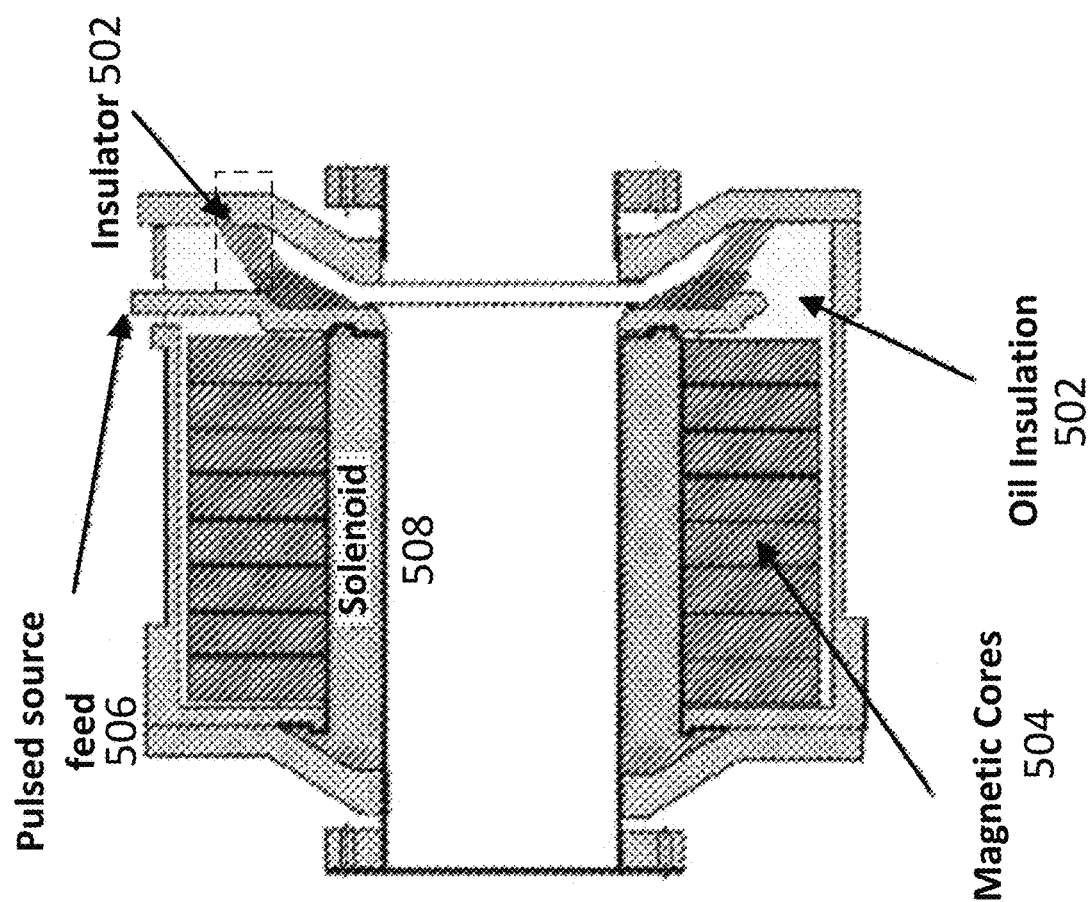
FIG. 5 illustrates a side view of components of an induction linear accelerator.

Several less than complete approaches by those highly skilled in the art of radiation therapy have been proposed and studied. Some of these were described earlier in this patent document. But unfortunately, all of the attempts, while potentially meeting some, do not meet all of the aforementioned demanding requirements. FIG. 5 illustrates a side view of components of an example induction linear accelerator (e.g., as shown in FIGS. 2A-B). Previous LIA accelerator cavities stacked the insulator along the axis with the magnetic cores. In this configuration, when a pulsed voltage is applied to the pulsed source feed (506), the magnetic induction created by the current flowing on the internal wall creates an accelerating potential across the insulator 502. Electrons in the gap next to the insulator 502 are therefore accelerated so long as the potential is maintained during the pulse. The solenoid (508) keeps the electrons focused along the accelerator. The geometry shown in FIG. 5 allows concertation of the accelerating electric field axially to provide additive focusing of the beam and control of the particle trajectories. For high currents, the configuration in FIG. 5 also allows RF energy created by the head of the beam to cause the volume around the insulator to oscillate and eventually perturb the tail of the beam. One of the disadvantages of this configuration is that the pulsed source modules can cause unwanted sporadic oscillations along the ferrite cores. In addition, this configuration also leads to a waste of space to obtain the desired acceleration gradient because the insulator material 502 is positioned co-axially with the magnetic cores 504, leading to increased cavity length.

Figure 6:
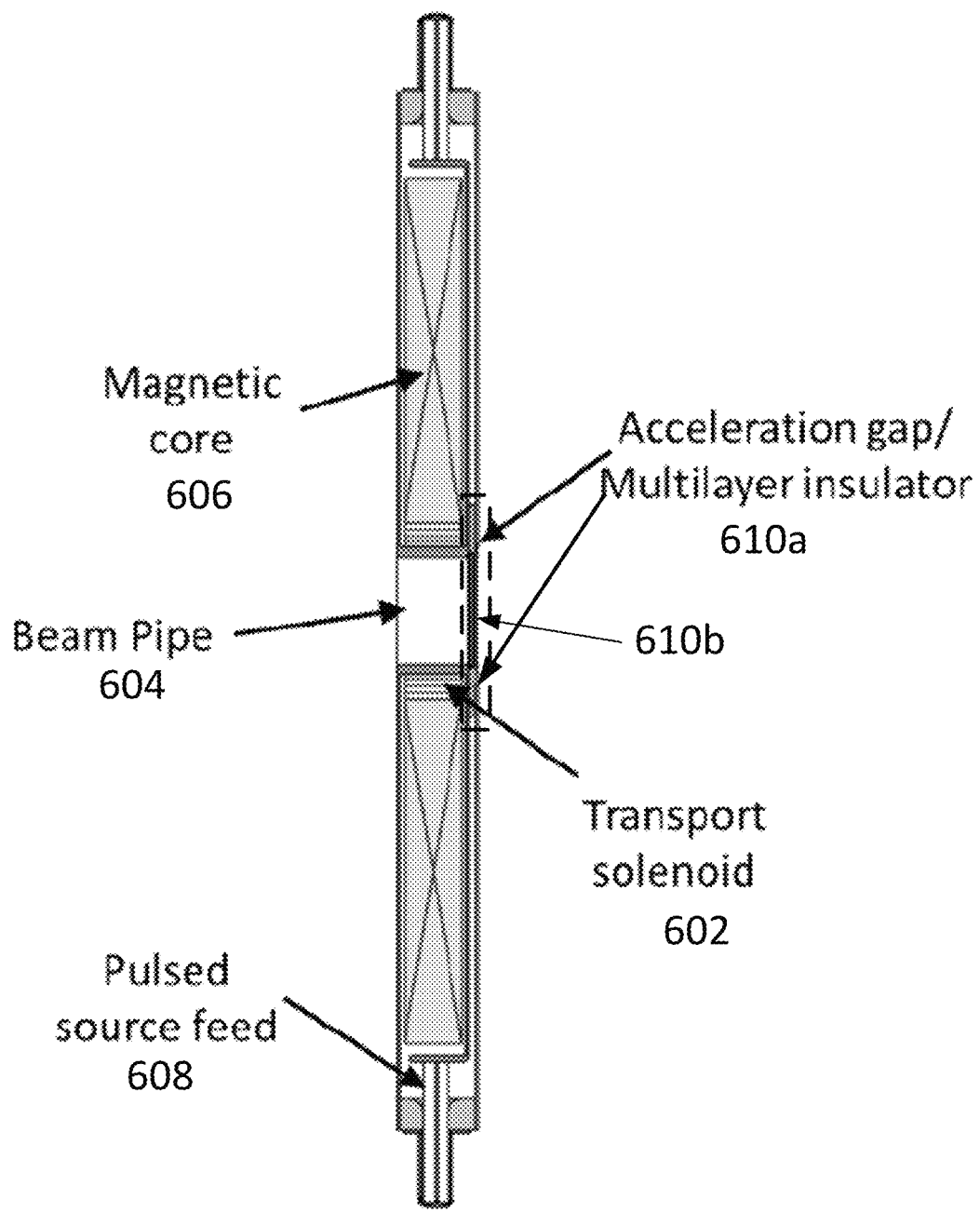
FIG. 6 illustrates an example configuration of the magnetic cores in accordance with one or more embodiments of the present technology.

To achieve a more efficient allocation of the cavity length, the higher gradient structure like the multilayer insulator is used along the beam pipe where the electric field is high. FIG. 6 illustrates an example configuration of the magnetic cores in accordance with one or more embodiments of the present technology. In this example, the multiplayer insulator 610*a,b* is positioned close to the beam pipe 604 and the solenoid 602. A first portion of the multilayer insulator 610*a*

(e.g., a cross section of a cylindrically shaped cell) is positioned right next to the beam pipe 604 and/or the solenoid 602, thereby minimizing stray particles causing avalanches and allowing gradients on the order of the Hansen type microwave driven linear accelerators to be achieved. A second portion of the multiplayer insulator 610b (e.g., a non-cross section portion) is also positioned proximate to the beam pipe. This configuration can provide a more compact design of the system. As part of this compact configuration, the pulsed source feeds 608 provide connectivity to the pulsed voltage source and are positioned along radial directions with respect to the pipe 904 and the magnetic cores 606. In the geometry shown in FIG. 5, as the beam propagates along the axis, the tail of the beam can eventually hit the beam pipe walls and be lost. In the configuration shown in FIG. 6, however, the volumes around the insulator are significantly smaller, preventing these types of oscillations. The multilayer insulator also acts as a filter for this oscillation, inhibiting their formation all together. It is noted that components in FIG. 6 that are not specifically described provide similar functionality as those in FIG. 5. The configuration shown in FIG. 6 can be applied to induction linear accelerators such as shown in FIGS. 2A-B.

Some testing of short pulsed accelerators has been performed. For the particular system of an H+ ion injector, the cavities were operated at 42 kV per cavity using a 30 ns pulse from a solid-state pulsed source. Insulation was $SF_6$. Shorter pulses for the same volt-second product and modification of the internal insulation would allow these cavities to achieve >3-MV/m.

Figure 7:
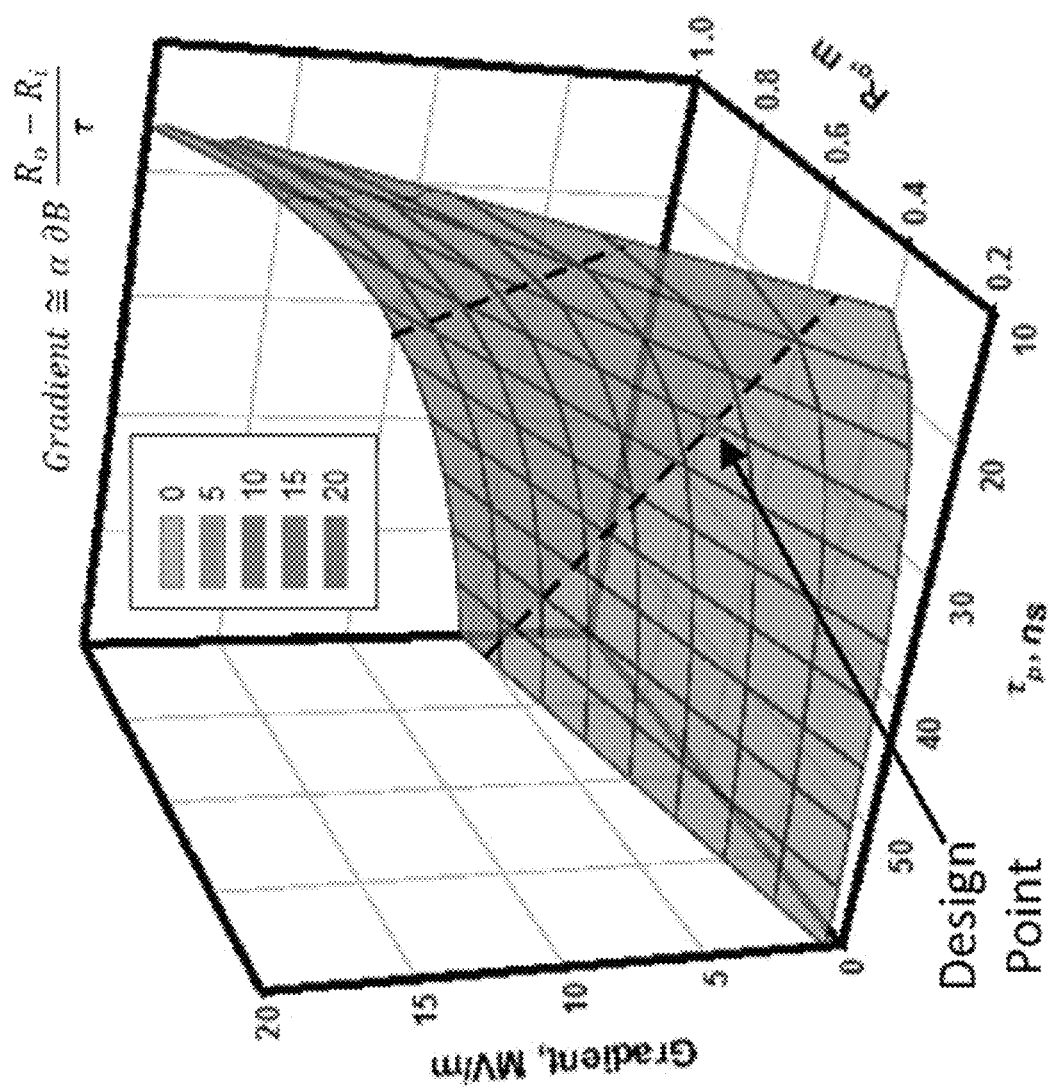
FIG. 7 illustrates example point design considerations in a high gradient induction cavity design based on volt-second properties of the core and the dimensions in accordance with one or more embodiments of the present technology.

FIG. 7 illustrates example point design considerations in a high gradient induction cavity design based on volt-second properties of the core and the dimensions in accordance with one or more embodiments of the present technology. In FIG. 7, $\alpha$ represents the cavity packing efficiency, $\partial B$ represents the flux swing of the magnetic core, $R_i$ represents the core inner radius, $R_o$ represents the core outer radius, and $\tau$ represents the accelerator pulse width. For this particular design point, take $R_i$=0.1-m, $\partial B \approx 0.6T$ (NiZn ferrite), and $\alpha$=60%. The point design estimate was based on conversion of the electrons to Bremsstrahlung using the dose rate scaling ($\propto I \ V^{2.6}$, where I is the beam current and V is the electron energy). Many existing systems, such as the Hansen type systems, were designed for around 0.3-A peak current with at least one published design for up to 1.2-A peak current. At this high current, the entrance gradient of the accelerator starts at about 12.7-MV/m, but at the 1.1-m exit, the gradient drops to 2.5-MV/m. The total energy gain is 10.5 MeV. For consistent comparison, the designed gradient of 12.7-MV/m, which is a constant, has been used. That case occurred at a reduced beam current of 0.34-A.

Gradient in an LIA is very dependent on the characteristics of the magnetic core. The core contributes the greatest volume dependent scaling parameter to the gradient of an induction accelerator cavity. Other than the cross-sectional area, the characteristics of a given core are dependent on the measured physical property, $\partial B$, measured in Tesla (T). This property is a measurement of the full excursion of the magnetic field in the core from a negative to a positive saturation state. The higher the $\partial B$ of a given material, the more compact the core and the higher the gradient.

Pulsed core saturation dynamics is a highly complex subject. Models have ranged from full implementation of multiparameter hysteresis formalism to phenological approaches based on Landau and Lifshitz theory. The latter of these approaches enables reduction of the model to a simplified dynamic network. While high aspect ratios in large cores can have non-uniform effects, saturation was treated only as a simple electromagnetic diffusion problem for this first order estimate.

High $\partial B$ materials such as Metglas can have large excursions of about 2.5-T whereas NiZn ferrite materials are typically around 0.6-T. Metglas requires long diffusion of the magnetic field into the material because of the high conductivity. Thin layers can allow faster bulk diffusion on the order of the necessary rise-time of the drive pulse. However, material availability is inconsistent. NiZn ferrites on the other hand are made from a suspension of fine magnetic particles that decreases the bulk diffusion time and are more widely available; pulse rise-times <10-ns have been demonstrated in large LIA cavities. For this estimate, the more conservative NiZn ferrite material is selected.

Another aspect to be considered is the packing efficiency, $\alpha$, of the induction cavity. Referring back to FIG. 6, the cross section that includes the multilayer insulator comes with increased internal complexity compared to an iris loaded cavity (e.g., as shown in FIG. 5). The complexity is accounted for using the $\alpha$ term that lowers the total gradient. For this particular estimate, a conservative value of 60% is assumed.

Finally, the inner and outer radii, $R_i$ and $R_o$ respectively, of the core defines the flux area for the magnetic field (for a given core thickness). While minimizing the inner radius and maximizing the outer radius increases the gradient, there are practical aspects to selecting the core size. For instance, large cavities tend to require multiple pulsed source feed points to ensure uniform excitation. In addition, care must be taken to ensure unwanted electromagnetic modes do not exist or are suitably damped in the larger structures.

Figure 8:
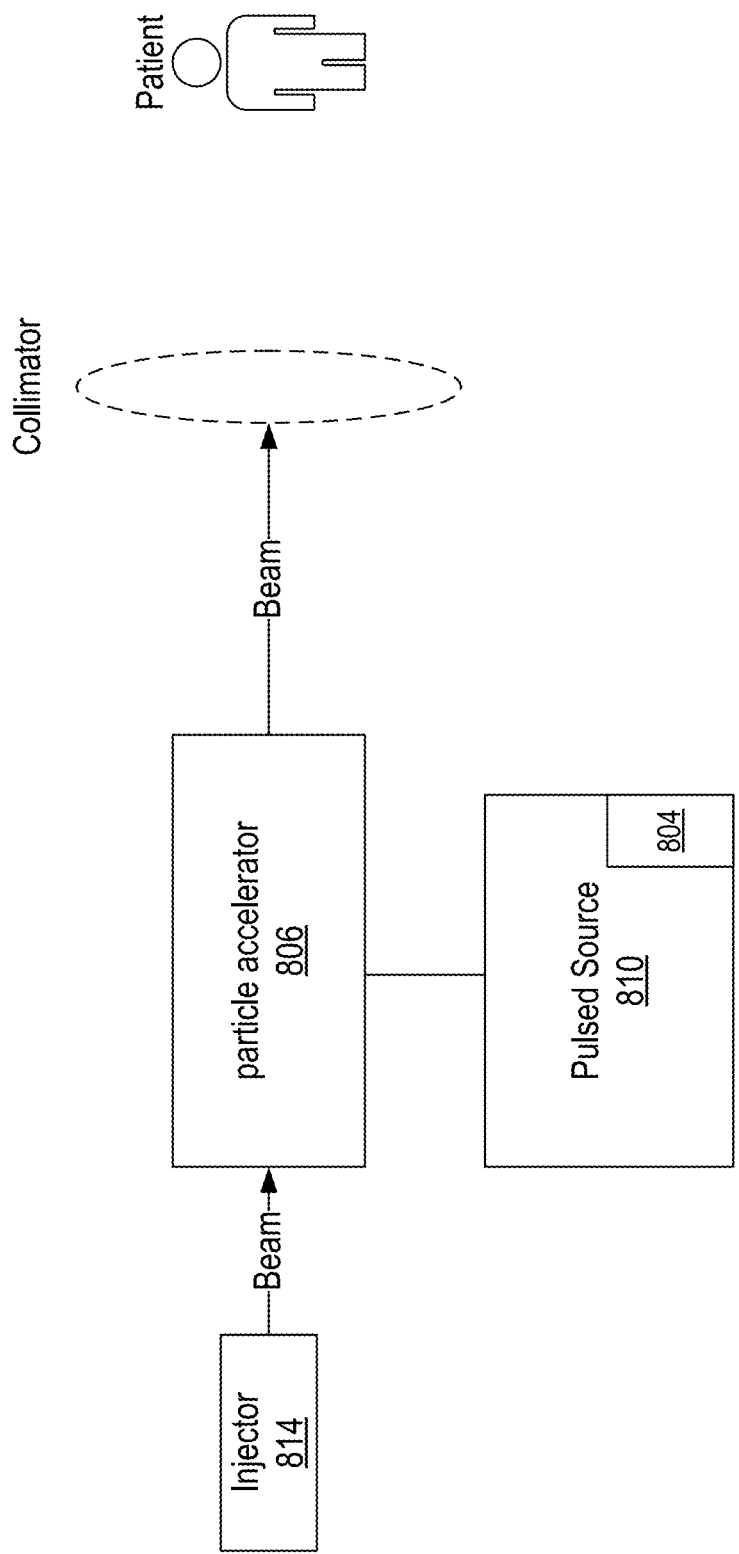
FIG. 8 illustrates an example configuration of an example radiotherapy system in accordance with one or more embodiments of the present technology.

FIG. 8 illustrates an example configuration of an example radiotherapy system in accordance with one or more embodiments of the present technology. The system includes a controllable switch (e.g., photoconductive switch) 804 that is coupled to a voltage source (e.g., a high-voltage source with one or more capacitors or another source capable of producing voltage values in the range 10-100 kV. The voltage source can be coupled to a first and a second electrode of the controllable switch 804 to establish an electric field across the switch 804. In an embodiment, the controllable switch 804 is implemented as a photoconductive switch such as an OTV device that includes a crystalline material that exhibits a substantially linear transconductance in response to receiving light from the light source. The light source can include one or more lasers that are operable to excite the charge carriers in the crystalline material and to cause the switch to operate. An injector 814 supplies a beam of particles (e.g., electrons or any charged particle useful for ultra-high dose rate therapy) to the particle accelerator 806. The photoconductive switch 804 is contained within a pulsed source 810 and coupled to the particle accelerator 806 and supplies the appropriate number of pulses of particular shape, amplitude, duration and duty cycle to accelerate the charged particles. By controlling the pulses supplied to the particle accelerator 806 from a pulsed source 810 (e.g., via the controllable switch 804), a specific dose rate, average dose and/or beam energy can be delivered to the target 816 (e.g., patient). That is, the system in FIG. 8 allows control of accelerator energy, current and/or dose rate using the controllable switch 804 by, for example, actively controlling the conductance of the switch and/or on-off times of the switch. In some embodiments, a radiation measurement device can also be incorporated into the system where the measured radiation can be used as a control feedback to modify the activation of the controllable switch 804 and to modify the voltage pulses that are output from the controllable switch 804. It should be noted that in example embodiments of the radiotherapy systems, a pulsed source feeds the accelerator directly without using an intermediate RF producing system to feed the accelerator.

Figure 9:
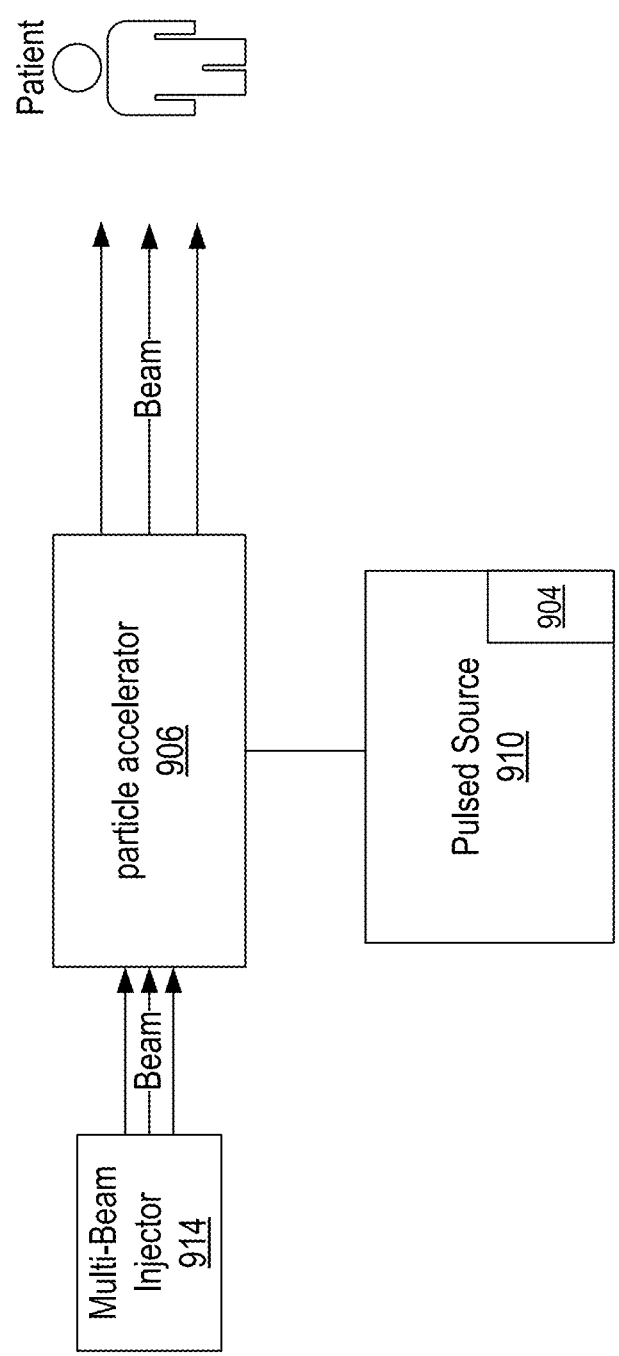
FIG. 9 illustrates an example configuration of an example multi-beam radiotherapy system in accordance with one or more embodiments of the present technology.

In some embodiments, multiple beams can be accelerated through a single cavity so that more than a single line of sight can be realized without the use of multiple accelerators. Because the gradient in an induction linear accelerator is not dependent on the beam pipe diameter, it can be made arbitrarily large. This unique feature enables the acceleration of multiple beams through the same accelerator. Thus, by creating multiple beamlets at the entrance of the accelerator, these beamlets can be transmitted separately in parallel to "catcher" optics to extract the beamlets and keep them separate. As separate beamlets, they can then be directed to the patient from multiple angles with various bending optics. FIG. 9 illustrates an example configuration of an example multi-beam radiotherapy system in accordance with one or more embodiments of the present technology. The system includes a photoconductive switch 904 that is coupled to a voltage source. The photoconductive switch 904 is implemented as an OTV device that includes a crystalline material that exhibits a substantially linear transconductance in response to receiving light from the light source. A multi-beam injector 914 supplies multiple beams to the particle accelerator 906.

The iris loaded linear accelerator used in conventional radiotherapy, while it could possibly be configured for such an arrangement, is less practical. Since this type of accelerator needs to be treated as a waveguide structure, the inner iris radius, where the beam is being accelerated, needs to be enlarged. This enlargement lowers the impedance of the structure and requires increased RF power for a given gradient. The advantage of the previously described induction linear accelerator is that the acceleration gradient is largely independent of the inner radius. So, enlargement of the beam pipe to accommodate multiple beams will have little effect on the power requirements. Such an approach of propagation of multiple beams in induction accelerators has been studied for use in heavy ion fusion systems, and can be similarly implemented in the disclosed FLASH radiotherapy systems as noted above.

A larger beam pipe radius enables the potential of creating multiple separate beams within the same accelerator and directing them to suitable collimators. The accelerator and the ancillary components are the greatest contributors to volume and cost in a treatment system. Accelerating multiple beams through a single accelerator and then using final optics to separate and guide the beams to the conversion target would result in significant savings for a conformal system.

To allow enough room for multiple beams while keeping the cavity small to avoid unwanted modes, a ferrite with inner radius of 10 cm and outer radius of 45 cm is selected. These radii provide a gradient of 5 MV/m so that the overall active accelerator length is 4-m for a 20-MeV system. It is noted that the OTV can operate at extremely high pulse repetition rates, so other aspects are taken into consideration to determine the suitable parameters.

The pulsed sources for ETA-II were operated reliably at 5-kHz. Using that rate as the baseline for this design, a 20 Gy dose at 1-m can be delivered in a total time of 13-ms (650 pulses) using a beam current of 25-A in 25-ns pulses. Average dose rate exceeds the 100 Gy/s threshold for the more pronounced observed effect by approximately 50% but is controllable with beam current flexibility and/or pulse repetition rate. Higher dose rates are certainly possible and are well within the parameter space of the accelerator. The peak beam current is approximately seventy-five times that of the Hansen type accelerator at the same energy providing a much higher dose rate. The point design comparison is summarized in Table II below.

| Parameter | Iris Loaded | Induction Linear Accelerator |
| --- | --- | --- |
| Electron Energy (MeV) | 20 | 20 |
| Beam Current (A) | 0.34 | 25 |
| Pulse Width (s) | 5.00E−06 | 2.50E−08 |
| Pulse Repetition Frequency (Hz) | 400 | 5000 |
| Net Gradient (MeV/m) | 12.7 | 5.0 |
| Accelerator Length (m) | 1.57 | 4.0 |
| Inner Radius (cm) | 2.3 | 10.0 |
| Instantaneous Dose Rate (Gy/s) | 1.62E+04 | 1.19E+06 |
| Average Dose Rate (Gy/s) | 32.4 | 148.9 |
| Total Dose (Gy) | 20.0 | 20.0 |
| Time On (s) | 0.62 | 0.13 |

As shown in the table above, the radiotherapy systems disclosed herein are capable of meeting all five aforementioned requirements at least in-part by actively controlling the operation of the photoconductive switch that is operable in a substantially linear transconductance region. In particular, the disclosed systems can achieve instantaneous dose rates that exceed $1.8 \times 10^5$ Gy/s, can administer the required dose in less than 200 ms, with average dose rates between greater than 100 Gy/s, and can provide the entirety of the irradiated region with levels above both the instantaneous and average dose rates. Furthermore, the system can be implemented in a compact form that occupies less than 100 $m^3$.

In some embodiments, the disclosed radiotherapy systems can include a power supply for charging an energy storage apparatus, connected to a controllable switching means, connected to a means of creating radiation for FLASH radiation, whereby the radiation is created by the high voltage pulse applied to a set of electrodes. The system can also include a means of measuring the amount of radiation administered to a partial or entirety of the patient, whereby the switching means controls the dose by the pulse amplitude, the pulse width, or the number of pulses being administered. The combination of these elements produces a compact system that meets all of the five aforementioned requirements and is operable to flexibly meet the requisite dose rates and other operational conditions. For example, the described photoconductive switches have very high breakdown voltages. For instance, a piece of silicon carbide, used in the proper configuration, is capable of withstanding 20 kV over 0.3 mm thickness. The disclosed photoconductive switches are further characterized by short response times, typically on the 1-10 ns times or less, thus allowing the output pulses to be appropriately modulated and shaped to meet the above noted requirements. Furthermore, the switch has a relatively small footprint, typically less than 10 $cm^3$ that enable the system to be implemented within a 100 cubic meter facility.

FIG. 10 illustrates a set of example operations that can be carried out to produce an output radiation beam in a radiotherapy system in accordance with one or more embodiments of the present technology. At operation 1002, a beam of charged particles is received from a particle source at a particle accelerator of a particle accelerator system. The particle accelerator comprises a pipe configured to allow the beam of charged particles to pass through, a magnetic core positioned proximate to the pipe and coupled to a pulsed source, and a multilayer insulator positioned adjacent to the pipe and the magnetic core. The particle accelerator system further includes a photoconductive switch coupled to the particle accelerator that comprises a doped crystalline material that is configured to receive a voltage from an energy source to establish an electric field across the doped crystalline material. At 1004, a plurality of voltage pulses is produced by the photoconductive switch in response to receiving light that is incident on the doped crystalline material. At 1006, the beam of charged particles is accelerated by the particle accelerator based on the plurality of voltage pulses to produce one or more output radiation beams for flash radiotherapy.

In some embodiments, the photoconductive switch is configured to receive the light from a light source and to operate in response to the received light. The photoconductive switch is operable in a linear mode of operation in response to the received light. In some embodiments, the light source includes one or more laser sources.

In some embodiments, the one or more output radiation beams are produced to include radiation pulses with an instantaneous dose rate that exceed $1.8 \times 10^5$ Gy/s. A required dose in less than 200 ms is administered, and the one or more output radiation beams having radiation pulses with an average dose rate greater than 100 Gy/s are produced. An entirety of a target region is irradiated with levels above both the instantaneous dose rate and the average dose rate.

In some embodiments, a radiation amount administered to the entirety of the target region is measured. In some embodiments, an instantaneous dose rate or average dose rate of the one or more output radiation beams is modified based on the plurality of voltage pulses produced by the photoconductive switch.

In some embodiments, the particle accelerator is an induction linear accelerator. In some embodiments, the beam of charged particles comprise electrons. In some embodiments, the pipe is configured to accommodate multiple beams of charged particle beams. In some embodiments, the particle accelerator system has a three-dimensional footprint of less than or equal to 100 cubic meters, and the particle accelerator system is operated in a clinical setting.

Another aspect of the disclosed embodiments relates to an accelerator system for use in a radiotherapy system. The accelerator system includes a particle accelerator configured to receive charged particles from a pulsed source. The particle accelerator comprises a pipe configured to allow the charged particles to pass through as a beam, a magnetic core positioned proximate to the pipe and coupled to the pulsed source, a multilayer insulator positioned adjacent to the pipe and the magnetic core. The accelerator system also includes a photoconductive switch coupled to the particle accelerator and configured to supply the particle accelerator with a plurality of voltage pulses. The particle accelerator is operable to accelerate the charged particles based on the plurality of voltage pulses, and to produce an output beam comprising one or more radiation pulses for radiotherapy.

In some embodiments, the particle accelerator comprises a solenoid coupled to the magnetic core and is positioned proximate to the magnetic core and the multilayer insulator. The pulsed source is coupled to the magnetic core via the solenoid to enable the particle accelerator to receive the charged particles.

In some embodiments, the photoconductive switch includes a doped crystalline material that is configured to receive a voltage from an energy source to establish an electric field across the doped crystalline material. The photoconductive switch is configured to receive light from a light source and to operate in response to the received light, the photoconductive switch being operable in a linear mode of operation in response to the received light.

In some embodiments, the light source includes one or more laser sources. In some embodiments, the photoconductive switch is operable to modify one or more of an amplitude, shape, spacing, number or width of the plurality of voltage pulses supplied to the particle accelerator. In some embodiments, the accelerator system has a three-dimensional footprint of less than or equal to 100 cubic meters.

In some embodiments, the accelerator system is operable to produce output radiation pulses with an instantaneous dose rate that exceeds $1.8 \times 10^5$ Gy/s, administer a totality of the output radiation pulses that constitute a required dose in less than 200 ms, produce the output radiation pulses with an average dose rate greater than 100 Gy/s, and irradiate an entirety of a target region with levels above both the instantaneous dose rate and the average dose rate.

In some embodiments, the particle accelerator is an induction linear accelerator. In some embodiments, the charged particles comprise electrons. In some embodiments, the pipe is configured to accommodate multiple beams of charged particle beams.

While this document contains many specifics, these should not be construed as limitations on the scope of an invention that is claimed or of what may be claimed, but rather as descriptions of features specific to particular embodiments. Certain features that are described in this document in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a sub-combination or a variation of a sub-combination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

It is understood that at least some of the components of the disclosed embodiments may be implemented individually, or collectively, in devices comprised of a processor, a memory unit, an interface that are communicatively connected to each other. The processor and/or controller can perform various disclosed operations based on execution of program code that is stored on a storage medium. The processor and/or controller can, for example, be in communication with at least one memory and with at least one communication unit that enables the exchange of data and information, directly or indirectly, through the communication link with other entities, devices and networks. The communication unit may provide wired and/or wireless communication capabilities in accordance with one or more communication protocols, and therefore it may comprise the proper transmitter/receiver antennas, circuitry and ports, as well as the encoding/decoding capabilities that may be necessary for proper transmission and/or reception of data and other information.

Various information and data processing operations described herein may be implemented in one embodiment by a computer program product, embodied in a computer-readable medium, including computer-executable instructions, such as program code, executed by computers in networked environments. A computer-readable medium may include removable and non-removable storage devices including, but not limited to, Read Only Memory (ROM), Random Access Memory (RAM), compact discs (CDs), digital versatile discs (DVD), etc. Therefore, the computer-readable media that is described in the present application comprises non-transitory storage media. Generally, program modules may include routines, programs, objects, components, data structures, etc. that perform particular tasks or implement particular abstract data types. Computer-executable instructions, associated data structures, and program modules represent examples of program code for executing steps of the methods disclosed herein. The particular sequence of such executable instructions or associated data structures represents examples of corresponding acts for implementing the functions described in such steps or processes.

Only a few implementations and examples are described, and other implementations, enhancements, and variations can be made based on what is described and illustrated in this disclosure.

What is claimed is:

1. An accelerator system for use in a radiotherapy system, comprising:
   a particle accelerator configured to receive charged particles from a pulsed source, wherein the particle accelerator comprises:
      a pipe configured to allow the charged particles to pass through as a beam,
      a magnetic core positioned proximate to the pipe and coupled to the pulsed source, and
      a multilayer insulator positioned adjacent to the pipe and the magnetic core; and
   a photoconductive switch coupled to the particle accelerator and configured to supply the particle accelerator with a plurality of voltage pulses, wherein the particle accelerator is operable to accelerate the charged particles based on the plurality of voltage pulses, and to produce an output beam comprising one or more radiation pulses for radiotherapy,
   wherein the photoconductive switch includes a doped crystalline material that is configured to receive a voltage from an energy source to establish an electric field across the doped crystalline material, and
   wherein the photoconductive switch is configured to receive light from a light source and to operate in response to the received light, the photoconductive switch being operable in a linear mode of operation in response to the received light,
   wherein the accelerator system is operable to:
   produce output radiation pulses with an instantaneous dose rate that exceeds $1.8 \times 10^5$ Gy/s,
   administer a totality of the output radiation pulses that constitute a required dose in less than 200 ms,
   produce the output radiation pulses with an average dose rate greater than 100 Gy/s, and
   irradiate an entirety of a target region with levels above both the instantaneous dose rate and the average dose rate.

2. The accelerator system of claim 1, wherein the particle accelerator comprises:
   a solenoid coupled to the magnetic core that is positioned around the pipe, wherein the solenoid is positioned proximate to the magnetic core and the multilayer insulator, wherein the pulsed source is coupled to the magnetic core via the solenoid to enable the particle accelerator to receive the charged particles.

3. The accelerator system of claim 1, wherein the light source includes one or more laser sources.

4. The accelerator system of claim 1, wherein the photoconductive switch is operable to modify one or more of an amplitude, shape, spacing, number or width of the plurality of voltage pulses supplied to the particle accelerator.

5. The accelerator system of claim 1, wherein the accelerator system has a three-dimensional footprint of less than or equal to 100 cubic meters.

6. The accelerator system of claim 1, wherein the particle accelerator is an induction linear accelerator.

7. The accelerator system of claim 1, wherein the charged particles comprise electrons.

8. The accelerator system of claim 1, wherein the pipe is configured to accommodate multiple beams of charged particles.

9. A method for producing output radiation in a radiotherapy system, comprising:
   receiving, at a particle accelerator of a particle accelerator system, a beam of charged particles from a particle source, wherein the particle accelerator comprises a pipe configured to allow the beam of charged particles to pass through, a magnetic core positioned proximate to the pipe and coupled to a pulsed source, and an insulator positioned adjacent to the pipe and the magnetic core, wherein the particle accelerator system further includes a photoconductive switch coupled to the particle accelerator that comprises a doped crystalline material that is configured to receive a voltage from an energy source to establish an electric field across the doped crystalline material;
   producing a plurality of voltage pulses by the photoconductive switch in response to receiving light that is incident on the doped crystalline material; and
   accelerating the beam of charged particles by the particle accelerator based on the plurality of voltage pulses to produce one or more output radiation beams for flash radiotherapy,
   wherein the method further comprises:
   producing the one or more output radiation beams that include radiation pulses with an instantaneous dose rate that exceed $1.8 \times 10^5$ Gy/s,
   administering a required dose in less than 200 ms,
   producing the one or more output radiation beams having radiation pulses with an average dose rate greater than 100 Gy/s, and
   irradiating an entirety of a target region with levels above both the instantaneous dose rate and the average dose rate.

10. The method of claim 9, wherein the photoconductive switch is configured to receive the light from a light source and to operate in response to the received light, the photoconductive switch being operable in a linear mode of operation in response to the received light.

11. The method of claim 10, wherein the light source includes one or more laser sources.

12. The method of claim 9, further comprising:
   measuring a radiation amount administered to the entirety of the target region.

13. The method of claim 9, comprising:
modifying an instantaneous dose rate or average dose rate of the one or more output radiation beams based on the plurality of voltage pulses produced by the photoconductive switch.

14. The method of claim 9, wherein the particle accelerator is an induction linear accelerator.

15. The method of claim 9, wherein the beam of charged particles comprise electrons.

16. The method of claim 9, wherein the pipe is configured to accommodate multiple beams of charged particle beams.

17. The method of claim 9, wherein the particle accelerator system has a three-dimensional footprint of less than or equal to 100 cubic meters, and the method further comprises:
operating the particle accelerator system in a clinical setting.

\* \* \* \* \*